US006821118B2

(12) United States Patent
Schlussel

(10) Patent No.: US 6,821,118 B2
(45) Date of Patent: Nov. 23, 2004

(54) SALIVA EJECTOR

(76) Inventor: Herbert Schlussel, 10 Boxwood La., Monsey, NY (US) 10952

(*) Notice: Subject to any disclaimer, the term of this patent is extended or adjusted under 35 U.S.C. 154(b) by 107 days.

(21) Appl. No.: 10/190,233

(22) Filed: Jul. 8, 2002

(65) Prior Publication Data

US 2004/0043356 A1 Mar. 4, 2004

(51) Int. Cl.[7] .......... A61C 17/06

(52) U.S. Cl. .......... 433/96; 433/91

(58) Field of Search .......... 433/91, 93, 94, 433/95, 96

(56) References Cited

U.S. PATENT DOCUMENTS

| | | | | | |
|---|---|---|---|---|---|
| 1,447,020 | A | * | 2/1923 | Grunberg | 433/91 |
| 1,596,478 | A | * | 8/1926 | Bittenbender | 433/91 |
| 2,005,625 | A | * | 6/1935 | La Riche | 433/91 |
| 2,130,406 | A | * | 9/1938 | Angell | 433/91 |
| 2,571,856 | A | * | 10/1951 | Freedman | 433/80 |
| 3,101,544 | A | * | 8/1963 | Baughan | 433/94 |
| 3,373,492 | A | | 3/1968 | Batch | |
| 3,541,583 | A | * | 11/1970 | Deuschle | 433/96 |
| 3,758,950 | A | * | 9/1973 | Krouzian | 433/91 |
| 3,881,254 | A | * | 5/1975 | Epstein | 433/96 |
| 5,066,228 | A | * | 11/1991 | Doundoulakis et al. | 433/91 |
| 5,114,342 | A | * | 5/1992 | Young et al. | 433/95 |
| 5,441,410 | A | | 8/1995 | Segerdal | |
| 5,509,802 | A | * | 4/1996 | Whitehouse et al. | 433/95 |
| 5,690,487 | A | * | 11/1997 | Whitehouse et al. | 433/91 |
| 6,299,444 | B1 | | 10/2001 | Cohen | |

* cited by examiner

*Primary Examiner*—Ralph A. Lewis
(74) *Attorney, Agent, or Firm*—Stanley J. Yavner

(57) ABSTRACT

A saliva ejector construction prevents tissue at the bottom inside of the patient's mouth from being aspirated by the vacuum action of the saliva ejector, thereby preventing discomfort for the patient; and the structure of the saliva ejector provides a tissue contacting contour, so that it not only rests and acts comfortably at the bottom of the mouth but enables complete suctioning of the saliva. A saliva ejector tip provides the accomplishment of comfort and complete suctioning of the saliva by defining elongated, vertical openings, and a spherical surface to contact the patient's tissue.

11 Claims, 2 Drawing Sheets

SALIVA EJECTOR

FIELD OF THE INVENTION

This invention relates primarily to saliva ejector constructions for use by dentists on patients, and more particularly to such saliva ejectors which are comfortable for the patient, and yet which present an end configuration to almost completely remove saliva and cooling water for the drill from the inside bottom of the patient's mouth.

BACKGROUND OF THE INVENTION

Many types of saliva ejectors have been used in an attempt to provide an ejector that both protects the oral tissue of the patient, and is comfortable for that patient, as well as being an effective means for removing much of the saliva from a patient's mouth during dental procedures.

For decades now, many structures have been proposed for either or both of maintaining the efficiency of saliva ejectors, and providing comfort to the patient. For instance, valves have been installed for controlling the suction of such devices. Also, valve control schemes have been proposed. Furthermore, control holes and variations in sizes and shapes for the ejection passages have been designed.

More specifically, Segerdal has patented a saliva ejector to overcome the drawbacks known to exist in available saliva ejectors in order to provide comfort to the patient and to perform the ejection efficiently, in his U.S. Pat. No. 5,441,410. However, by Segerdal's installing a thin disk-like guard to prevent patient's discomfort by preventing aspiration of the patient's tissue at the bottom of the mouth, and since the disk is never exactly parallel to the bottom of the patient's mouth, the tissue is sometimes aspirated and still leads to discomfort problems for the patient.

Likewise, Batch has presented, in U.S. Pat. No. 3,373,492, a more elaborate compressible spring at the tip of the saliva ejector, which purportedly lowers the discomfort level for the patient.

In both of the above patented structures, the prevention of discomfort is neither as effective as the present invention, nor does it present a simplicity and efficiency of design as will become apparent for the present invention.

OBJECTS AND SUMMARY OF THE INVENTION

Accordingly, a primary object of the present invention is to provide a saliva ejector, which is simple in its construction, efficient in its operation and comfortable for the patient with which it is used.

A further and more particular object of the present invention is to provide a saliva ejector which makes use of the available basic design of saliva ejectors, but adds an element at the end thereof, which presents a curved rather than an edged surface for contact with the tissue inside and at the bottom of the patient's mouth, and yet presents a minimum additional tip protrusion toward the bottom of the patient's mouth, so as to make use of the vertical slots presently available for efficiently removing saliva accumulating at the bottom of the patient's mouth.

These and other objects of the present invention are provided in a saliva ejector which features disposability and simplicity of design and a significant reduction in the discomfort such an instrument provides to the patient. A typical saliva ejector features an elongated ejector tube, from the end of which, outside of the patient's mouth, a suction or vacuum capability is applied sufficiently to remove unwanted build-up of saliva at the bottom inside of the patient's mouth. As is usual with such instruments, at the other end, the tip of the passage for insertion to the patient's mouth is generally after a U-shaped bend and includes a tip opening surrounded by a plurality of vertical slots arranged perpendicularly to the plane of the opening. In the present invention structure, parallel to the plane of the opening, and slightly inward of the passage therefrom, a disk smaller than the diameter of the passage, is provided, to which is attached a sphere or a slightly egg-shaped sphere. If the long axis of an egg-shaped sphere is arranged perpendicular to the axis of the passage, and it is attached to the disk, only some of the egg-shaped element protrudes beyond the tip, where the vertical slots end. Likewise, if the attached element is truly spherical, the protrusion beyond the tip is also minimal. The protruded element thereby presents a completely rounded surface to provide virtually no discomfort to the patient; and since the aspiration by the suction takes place around the upper half of the sphere, which is inside the passage, such aspiration provides little if any discomfort to the patient, and yet efficiently removes saliva from the bottom inside of the patient's mouth.

BRIEF DESCRIPTION OF THE DRAWINGS

Other objects, features and disadvantages of the present invention will become apparent by reference to the following detailed description of a preferred, but nonetheless illustrative, embodiment of the present invention, with reference to the accompanying drawings, wherein.

DETAILED DESCRIPTION OF THE PREFERRED AND ALTERNATIVE EMBODIMENTS

Figure 2:
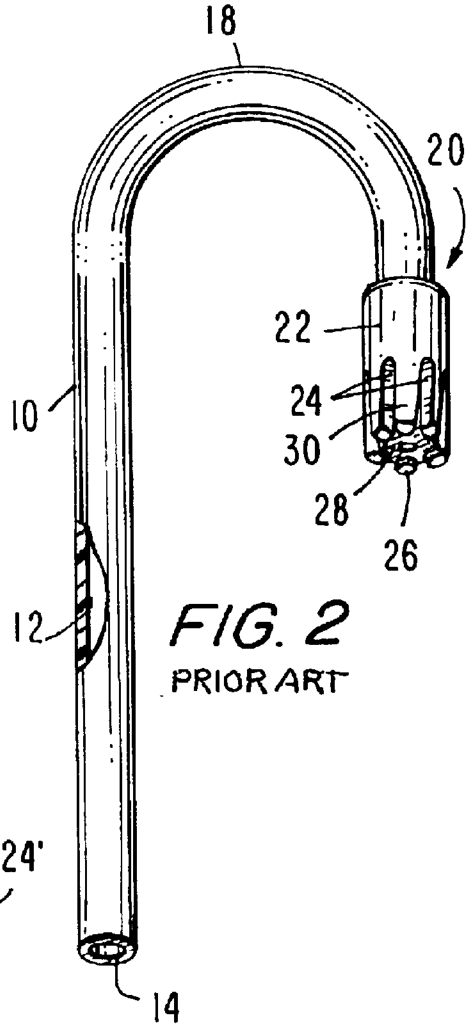
FIG. 2 is also an isometric view showing a commonly used ejector design, featuring vertical intake slots and a baffle or disk slightly inside of the end of the tip of the device.
Figure 4:
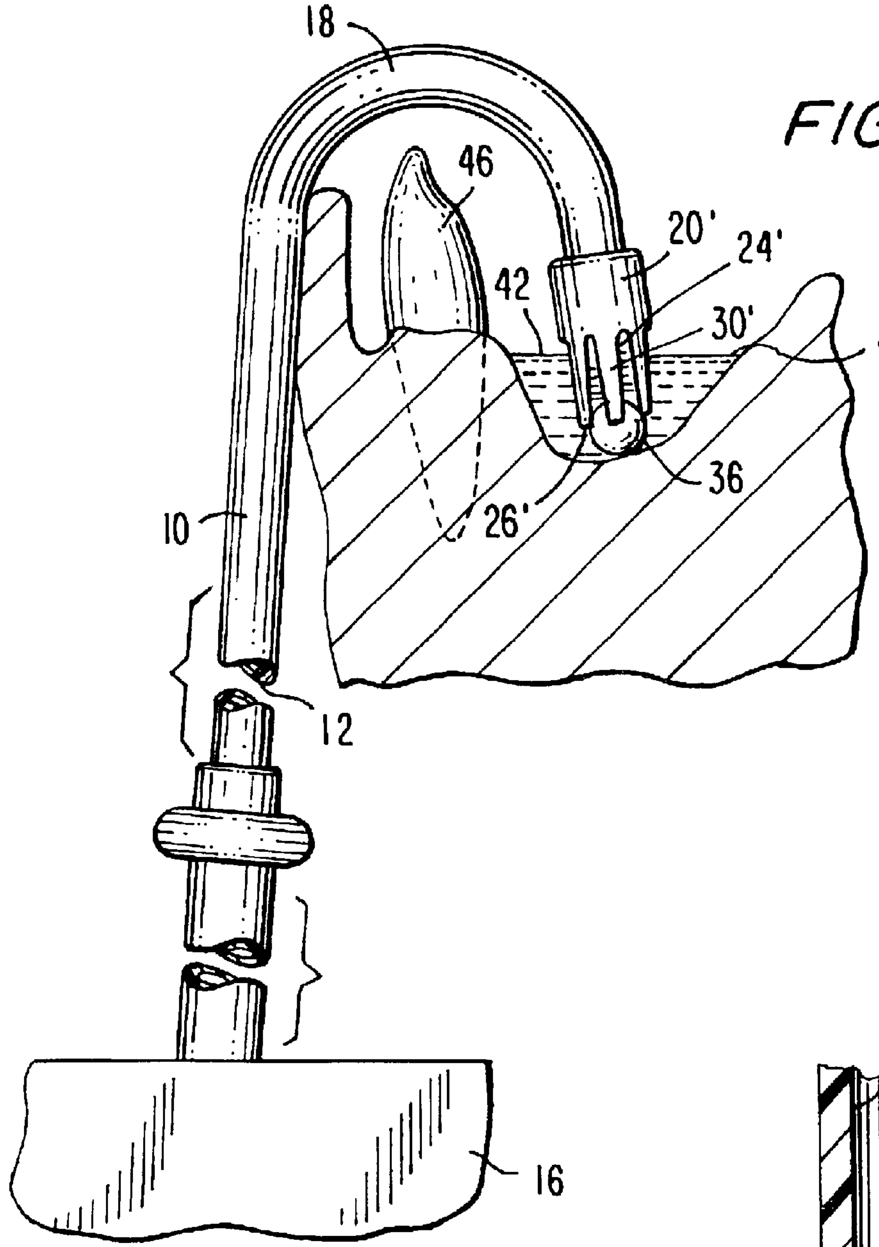
FIG. 4 shows the design of the present invention, as attached to the source for suction, and with the saliva ejector tip end contacting the tissue at the bottom of the patient's mouth, where saliva is ejected.

As may be seen from the prior art configurations discussed above, perhaps the most common form of a saliva ejector is shown in FIG. 2, with an ejector passage tube 10, defining an ejection passage 12 is connected at one end 14 to a source of suction 16 (FIG. 4). At point 18 of tube 10, usually a U-shaped bend is provided in order to place the instrument in a manner which provides the tip, generally designated 20, in the patient's mouth, with the balance of tube 10 depending downwardly from the patient's mouth.

Figure 1:
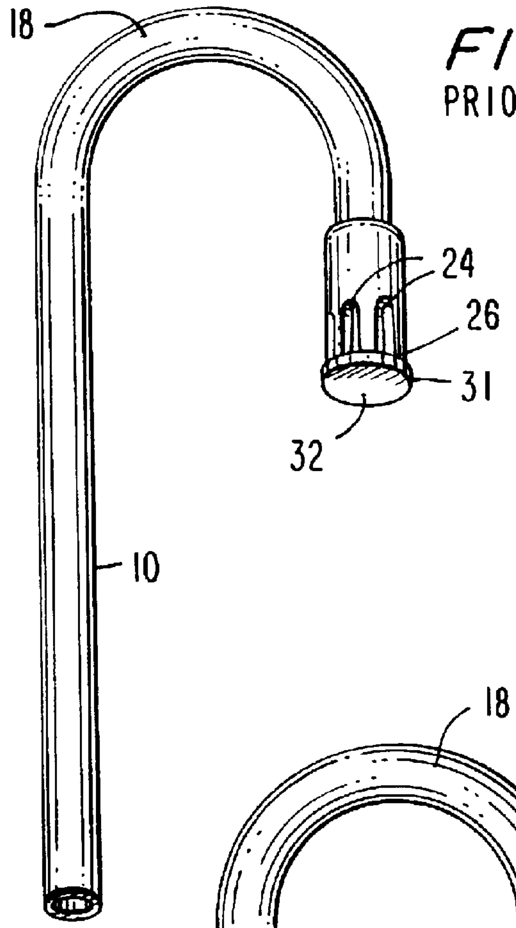
FIG. 1 represents a prior art saliva ejector, which adds to the common ejector a disk at the tip in order to prevent direct aspiration and contact between the ejector tip and the tissue of the patient, to minimize discomfort for the patient.

Usually, as is indicated in FIGS. 1 and 2, tip 20 includes a plastic tubular element 22, defining a plurality of vertical slots 24 toward tip end 26. Slightly inwardly of tip end (FIG. 2), a disk 28 is provided, usually attached to the inside surfaces of columns 30 separting the vertical slots 24. Less frequently, but not shown, one or two of the columns 30 protrudes inwardly of passage 12 to connect disk 28 in its position just inside ejector tip end 26. Also commonly, an opening (not shown) is provided at appoximately the center of disk 28 in order to attempt to increase the suction of the instrument, but usually such increase in suction through tube passage 12 is more uncomfortable for the patient.

FIG. 1 shows other prior art, wherein a thin disk 32 is placed at tip end 26 in order to prevent tissue aspiration into the instrument; but this type of design has served to increase, rather than decrease, patient discomfort by means of contact of edges 31 of disk 32 with tissue at the bottom of the patient's mouth, in addition to causing the aspiration of tissue when the disk, as is usual, is not exactly parallel to the bottom of the patient's mouth.

Figure 3:
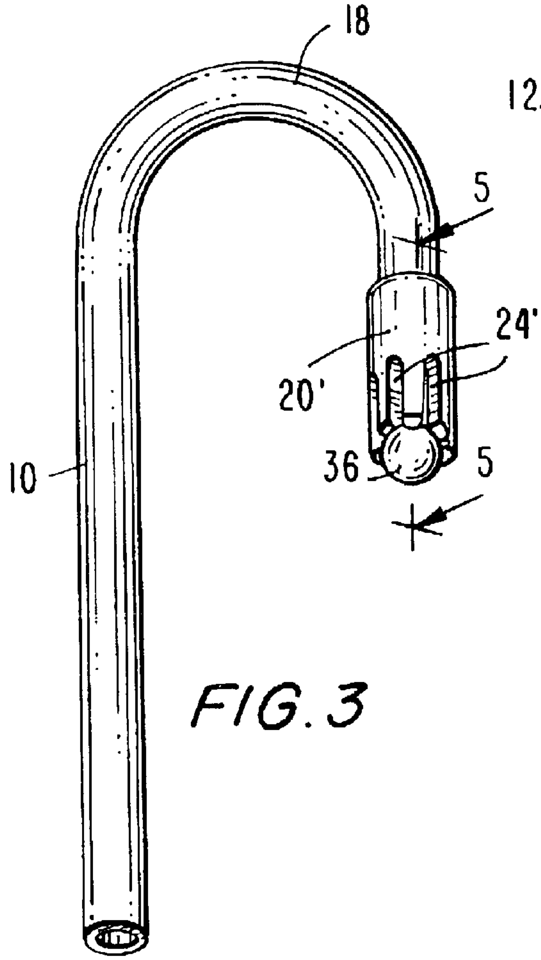
FIG. 3 is an isometric view showing the saliva ejector tip area of the present invention, wherein a sphere is attached to the disk just inside of the tip end, wherein a plurality of vertical slots are intact, with respect to the common design of FIG. 2, and wherein the spherical attachment at the tip end protrudes only somewhat beyond the tip end.
Figure 5:
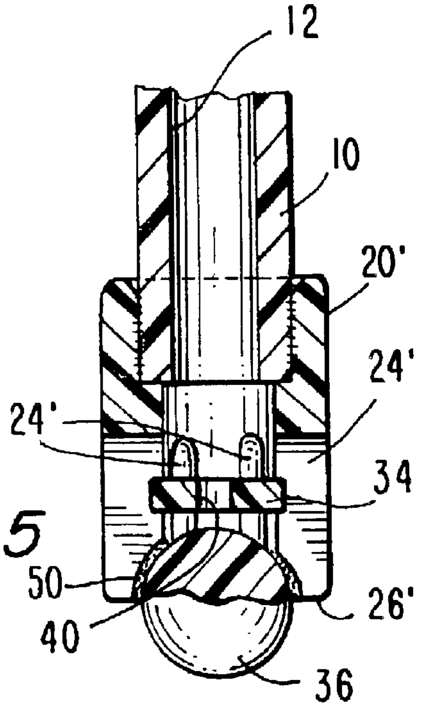
FIG. 5 is a sectional view, taken along the line 5—5 of FIG. 3 and showing the ejector passage, the vertical slots, the connection between the sphere and the disk slightly inward of the tip end, all to provide the satisfaction of objects of comfort and efficiency provided by the present invention.

FIGS. 3–5, showing the present invention, duplicates the use of tube 10, defining an ejector passage 12 for suction or vacuum. U-shaped bend 18 leads to tip 20'. Tip 20' defines vertical slots 24' supported by columns 30'. Disk 34 is located just inwardly of tip end 26'. An inlet element in the form of sphere 36 is preferably partially connected by adhesive 50 or molded together with some of columns 30 and/or with disk 34, so that sphere 36 depends below tip end 26'.

It should be noted, in the preferred embodiment—FIG. 5, that disk 34 defines a center opening 40 through which suctioned saliva flows after passing around the sphere 36. It may be seen (FIG. 4) that saliva 42 at the bottom of a patient's mouth is usually well inwardly of tip end 26', and the unwanted aspiration resulting from direct contact of tissue 44 with suction through passage 12 is prevented by sphere 36, and yet the flow around sphere 36 is sufficient to efficiently suction saliva 42 into the instrument, so that the dentist has clear and effective access to the patient's teeth 46.

The above construction of the present invention, although of simple design, satisfies the objectives of the dental profession, as well as the objectives of their suppliers. When in use, the instrument is comfortable for the patient in terms of tissue not being aspirated, and in terms of avoiding the general discomfort sometimes experienced with the prior art instruments for the same purpose with respect to the feel for the patient of concentrated suction against tissue. With the present invention suction takes place around the sphere 36, and yet the flow of saliva upwardly, by means of the suction, is smooth and even. The additional height of tip 20' of the present invention (when compared with prior art instruments) above the bottom of the mouth is minimally raised by approximately the amount of the diameter of sphere 36, so the effectiveness in removing saliva is every bit as good, if not better, than the prior art instruments discussed in the background for the present invention. As an alternative to the strictly spherical shape of sphere 36, it is readily seen that an egg shape with its major axis perpendicular to the axis of flow within tip 20', would be useful in the construction of the present invention with perhaps even less extension of the instrument below tip end 26'.

Although a complete description of preferred and alternative embodiments has been provided in the foregoing, the limitations for the present invention are set only by the following claims.

What is claimed is:

1. An elongated saliva ejector for use by a dentist with a patient comprising:

a substantially cylindrical and elongated ejector tube having a proximal first end for connection to a suction source, a distal second end, and an ejector passage defined between said ends, an ejector tip connected to said distal second end, said ejector tip defining a tip end distally of the distal second end of said ejector tube, said ejector tip having vertical columns for part of its length, said columns defining therebetween elongated slots, a disk located proximally of said tip end, and an inlet element defining a rounded side projecting distally of said tip end, said columns and slots terminating approximately at said tip end an said inlet element connected to some of said columns.

2. A saliva ejector according to claim 1, wherein said inlet element defines a spherical shape.

3. The saliva ejector of claim 1 wherein the inlet element is connected proximate the disk.

4. The saliva ejector of claim 3, wherein the inlet element defines a spherical shape.

5. An elongated saliva ejector for use by a dentist with a patient, comprising a substantially cylindrical and elongated ejector tube having a proximal first end for connection to a suction source, a distal second end, and an ejector passage defined between said ends, an ejector tip of circular cross-section connected to said distal second end of said ejector tube, said ejector tip having elongated columns for part of its length, said columns defining therebetween elongated slots, and an inlet element defining a rounded side projecting distally of said columns and said slots, and connected to some of said columns, the least diameter of said rounded side being distal of and less than the diameter of the column portion of said ejector tip, to separate said columns and said slots from the mouth tissue of said patient and thereby mitigate tissue aspiration and promote efficient saliva flow during saliva removal.

6. The saliva ejector of claim 5, wherein said ejector tip defines a substantially cylindrical shape.

7. The saliva ejector of claim 5, wherein the inlet element defines a spherical shape.

8. A saliva ejector for use while treating a dental patient having mouth tissue and saliva comprising:

an ejector passage tube having a first end and second end and connectable at said first end to a suction source;

a substantially cylindrical ejector tip coupled to the second end of said ejector passage tube, the ejector tip defining a proximal end, a distal end, and a plurality of openings to permit a flow of saliva into the ejector passage tube; and an inlet element defining a rounded side projecting distally from the distal end of the ejector tip, the least diameter of said rounded side being distal of and less than the diameter of the portion of said cylindrical ejector tip having said openings, to separate the plurality of openings from the patient's mouth tissue to thereby mitigate tissue aspiration and promote efficient saliva flow during saliva removal.

9. The saliva ejector of claim 8, wherein the ejector tip includes a plurality of spaced vertical columns for part of the length thereof, defining said plurality of openings.

10. The saliva ejector of claim 9, wherein the inlet element is a sphere that is connected to at least two of the plurality of spaced vertical columns such that the inlet element continually separates the plurality of spaced vertical columns from mouth tissue during saliva removal.

11. A saliva ejector for use in treating a dental patient having mouth tissue, for coupling to a suction source to facilitate removal of saliva from said mouth tissue, the saliva ejector comprising:

a substantially cylindrical ejector tube, defining a passage and having proximal and distal ends, a substantially cylindrical ejector tip at said distal end of said saliva ejector tube constructed to permit a flow of saliva into said passage, and an inlet element coupled to said ejector tip, the inlet element having a rounded side projecting distally from said ejector tip, the least diameter of said rounded side being distal of and less than the diameter of said substantially cylindrical ejector tip to separate the ejector tip from mouth tissue in order to mitigate tissue aspiration and promote efficient saliva flow during saliva removal.

* * * * *